(12) United States Patent
Mangold et al.

(10) Patent No.: US 7,163,745 B2
(45) Date of Patent: Jan. 16, 2007

(54) ODOR ADSORPTION AGENT IN HYGIENE ARTICLES

(75) Inventors: Rainer Mangold, Herbrechtingen (DE); Klaus Hermann, Giengen (DE)

(73) Assignee: Paul Hartmann AG, Heidenheim (DE)

( * ) Notice: Subject to any disclaimer, the term of this patent is extended or adjusted under 35 U.S.C. 154(b) by 0 days.

(21) Appl. No.: 10/467,564

(22) PCT Filed: Feb. 7, 2002

(86) PCT No.: PCT/EP02/01279

§ 371 (c)(1),
(2), (4) Date: Aug. 8, 2003

(87) PCT Pub. No.: WO02/064176

PCT Pub. Date: Aug. 22, 2002

(65) Prior Publication Data

US 2004/0077239 A1    Apr. 22, 2004

(30) Foreign Application Priority Data

Feb. 10, 2001    (DE) ............................... 101 06 139

(51) Int. Cl.
*B02B 15/02* (2006.01)
*B02B 17/02* (2006.01)
*B31B 1/60* (2006.01)

(52) U.S. Cl. ...................... 428/403; 428/327; 428/328; 428/357; 428/364; 428/402; 428/407; 442/327; 442/417; 156/60; 156/279; 156/298; 156/308.2

(58) Field of Classification Search ................ 428/364, 428/403, 327, 328, 357, 402, 407; 442/327, 442/417; 156/60, 298, 279, 308.2
See application file for complete search history.

(56) References Cited

U.S. PATENT DOCUMENTS

| 4,525,410 A | | 6/1985 | Hagiwara | |
|---|---|---|---|---|
| 4,788,080 A | * | 11/1988 | Hojo et al. | ................. 427/204 |
| 5,256,476 A | * | 10/1993 | Tanaka et al. | ................. 442/1 |
| 5,498,478 A | | 3/1996 | Hansen | |
| 5,997,829 A | * | 12/1999 | Sekine et al. | ............... 423/210 |
| 6,376,741 B1 | * | 4/2002 | Guarracino et al. | ........ 604/359 |

FOREIGN PATENT DOCUMENTS

| DE | 691 22 086 | | 1/1991 |
|---|---|---|---|
| DE | 691 31 127 | | 1/1991 |
| DE | 695 17 799 | | 2/1995 |
| EP | 0 392 528 | | 10/1990 |
| EP | 0 882 485 | | 12/1998 |
| EP | 1 034 800 | | 9/2000 |
| JP | 41-0127450 A | * | 5/1998 |
| WO | WO 01/05583 | | 1/2001 |

* cited by examiner

*Primary Examiner*—Norca L. Torres-Velazquez
(74) *Attorney, Agent, or Firm*—Young & Basile, P.C.

(57) ABSTRACT

An odor adsorption agent, in particular for use in a hygiene article, is formed of a thermoplastic granulate and a zeolite bonded to the thermoplastic granulate by means of a welded bond.

19 Claims, 2 Drawing Sheets

ODOR ADSORPTION AGENT IN HYGIENE ARTICLES

This application is a 371 of PCT/EP02/01279 Feb. 7, 2002.

BACKGROUND

The present invention relates to an odor adsorbing agent which is intended to find an application in the area of hygiene articles, such as diapers, sanitary napkins, tampons and other incontinence articles. The odor adsorption agent is intended to have the capability of combating a broad spectrum of unpleasant smelling odors.

Hygiene articles are very often designed not only with the purpose in mind that they should have the best possible absorption capability for body fluids, such as blood, menses and urine, but beyond that with respect to their hygienic characteristics and their comfort in use. Disposable products such as diapers and panty liners normally consist of a fluid-permeable topsheet, an absorbent core and a fluid-impermeable backsheet. Hygiene articles exist in the widest variety of sizes, shapes and thicknesses.

One particular aspect of this type of hygiene article is the control of resulting odors. Many body fluids have the unpleasant characteristic of emitting an odor, or, in conjunction with air or bacteria, of generating a similar odor for a prolonged period.

From the prior art, a wide variety of materials is known as an odor adsorbent. Zeolites in particular are used for this purpose. Zeolites are normally used in the form of small particles, so that the zeolite material is present in powder form. A zeolite powder of this kind has the disadvantage that it is difficult to handle in industrial settings. Zeolite powders tends to create dust and additionally have the characteristic of detaching, or separating out, from the absorbent structure of the hygiene article in which they are contained. This is particularly the case with the high processing speeds which are prevalent on modem machines producing diapers, for example.

Thus it is known from the prior art to combine zeolites with amorphous silicic acid into agglomerates.

Furthermore it is disclosed in the prior art, for example in EP 0 515 477 B1, to bond zeolites to the absorption means, such as a superabsorbent polymer, by means of chemical bonds. However, as a result of this bond the SAP characteristics, and thus the absorption characteristics for body fluids are changed. The bond takes place in the form of a cohesive mixture with the addition of a binder, specifically hydroxypropyl cellulose.

A further disadvantage of the binding of zeolite to SAP is that the zeolite can only be added in metered quantities together with the SAP, but the anchoring of the zeolite to the SAP is weak. If the bond between zeolite and SAP is broken, the known dust problems re-occur. It is further known, for example, from PCT/US/99/02760 to bond zeolites into a polymer matrix, where the matrix has a polymer of functional groups which react with the zeolite and as a result bind it to themselves.

Finally, it is known from DE-OS 21 64 262 to bond adsorbents to "bi-component fibers". These fibers are, for one, expensive in production and, secondly, difficult to incorporate into the absorbent structure of a hygiene article.

The object of the invention is to prepare an odor adsorption agent and a hygiene article and a method for producing an odor adsorption agent which is simple to handle on an industrial scale, has good odor adsorption capability and is particularly suitable for use in hygiene articles.

SUMMARY

The invention achieves this object by preparing an odor adsorbing agent comprising a thermoplastic granulate and zeolites bonded to the thermoplastic granulate by means of fused bonds. The zeolites are fused to the thermoplastic granulate in this process. A material combination of this type is particularly well suited to be admixed to the SAPs (superabsorbent polymers) normally used in the hygiene industry. Specifically, no additional metering equipment is required for the admixing.

The zeolites are silicate frameworks in which corner-linked $[(AlSi)O_4]$ tetrahedra are present as polyhedra, layers or chains, the tetrahedra being linked into a highly porous, anionic network of cavities permeated by long channels. One potential application for zeolites is as molecular sieves. The zeolites used here should not be of the fibrous type, since they conceal safety risks, similar to asbestos. In addition, the zeolites preferred here are largely hydrophobic, since they are normally intended to absorb odors in the presence of body fluids.

The odor adsorption capability of these zeolites configured as molecular sieves is created by the capture of malodorous substances through chemical adsorption within their molecular structure. It is important that the internal cavities or lattices of the zeolite molecules are open and available for the odor-causing molecules.

By binding the zeolites, which generally have a very small particle size, to larger particles, namely a thermoplastic granulate whose particle size can easily be adjusted, the usual handling problems with zeolites, such as dust creation and separating out, can definitely be prevented.

By binding the zeolites to the thermoplastic granulate by fusion bonds, the zeolites are first of all securely anchored to the granulate, but there is no chemical change either in the granulate or the zeolite, so that the adsorption characteristics of the zeolites are fully preserved. In addition, the surface of the zeolites is reduced by only a small amount as the result of the adhesive fusion binding.

Finally, the binding can be implemented with simple technology. Polypropylene, polyethylene, polyamide or EVA in particular can be considered as the thermoplastic granulate.

The zeolites are preferably smaller and specifically very much smaller than the particles of the thermoplastic granulate to which they are adhered by means of fusion binding. As a result, a great many zeolite particles can be bonded to a single granulate particle. Specifically, the size of the granulate can be ten times, specifically one hundred times and specifically more than one hundred times the size of the zeolite particles.

The granulate can have a particle size of 50 to 2,000 µm, specifically from 100 to 1,000 µm and specifically from 200 to 800 µm. In contrast, the zeolites preferably have a particle size from 0.1 to 50 µm and specifically from 1 to 10 µm. In this size range, particularly good, effective odor adsorption exists, particularly for the odor-causing molecules of body fluids.

The combination of a thermoplastic granulate with a particle size of 200 to 800 µm with zeolites having a particle size of 1 to 10 µm is particularly suited for use in the field of hygiene articles. This combination offers advantages with respect to the substrate surface, costs and adsorption of odor with respect to an effective use of zeolites and the ability to dispense them in controlled quantities into hygiene articles.

Suitable zeolites are, for example, the zeolite from the UOP Company, which is marketed under the Abscents 3000 name, or the zeolite from the Degussa Company, which carries the brand name Flavith S108.

The invention further relates to a hygiene article, specifically a sanitary napkin, a diaper or a tampon, comprising a previously described odor adsorption agent.

The use of an odor adsorption agent is particularly recommended in hygiene articles and increases the comfort of the said hygiene article for the wearer. Many of the body fluids secreted have an unpleasant odor at least in contact with air and bacteria, which can be limited or prevented by the addition and use of odor adsorbers.

Provision can be made for the hygiene article to comprise an absorbent structure which has a superabsorbent polymer as the absorbing agent for the body fluid to be contained. Such superabsorbent polymers (SAP) are frequently used in hygiene articles because of their outstanding storage and binding characteristics for fluids. In the case of SAPs, they are gel-forming polymers which are converted into a gel form as the result of swelling from their original powder form through contact with water.

Many times the amount of fluid can be bound safely and quickly. The risk of rewetting is clearly reduced.

The superabsorbent polymer can exist in granulate form. The superabsorbent polymer and the odor adsorption agent can be present as a mixture in the hygiene article. This offers the advantage that they can be supplied and metered to the absorbent core together. Additional metering equipment is not required.

A separate metered supply can also be provided. In this way particularly simple recipes with different odor adsorption characteristics can be manufactured. Equipment such as is known and customary for SAP metering are suitable for added metered quantities. Specific provision can be made for the superabsorbent polymer and the odor adsorption agent to be disposed in layers in the hygiene article.

Particularly advantageous properties with respect to the mixing characteristics result if the particle size of the SAP and those of the odor adsorption agent are essentially the same. The invention further relates to a process for producing an odor adsorption agent as described in what preceded. The thermoplastic granulate is superficially softened in a heatable mixer as the substrate, and the zeolites are added in metered quantities to the granulate. They adhere to the softened shell of the granulate by means of fusion bonds.

The mixing motion can continue as cooling proceeds until the shell of the granulate is essentially hardened to prevent the granulate elements from adhering to one another. The softening takes place only on the surface, whereby the core of the granulate remains hard. The zeolites adhere to the softened surface without penetrating too deeply into the granulate and thereby losing their odor adsorption capability.

As the temperature is lowered, the mixing or stirring motion should continue, because in particular with only a small zeolite charge, the granulate particles can otherwise adhere to one another.

Suitable mixers are known from the prior art and can be operated continuously or discontinuously.

BRIEF DESCRIPTION OF THE DRAWING

The invention will be explained more fully hereinafter using an example, in which.

DETAILED DESCRIPTION

In the example, a co-polyamide granulate was selected as the thermoplastic material, which is used as an adhesive melt for the textile industry, with a grain size from 200 to 500 μm and a melting point of 105° C. and an adhesion point of about 70° C.

With the assistance of a special mixer, which is configured as a discontinuous heated shear mixer, 10% zeolite was applied to the surface of a suitable substrate material. Abscents 3000 having a particle diameter of about 3 μm and Flavit S108 having a particle diameter of about 10 μm was applied as the zeolite. The Abscents 3000 zeolite is a zeolite from the UOP Company and the Flavith S108 is a zeolite from the Degussa Company.

Following an adequate heating phase the products were cooled in a downstream mixer and then removed.

Figure 1:
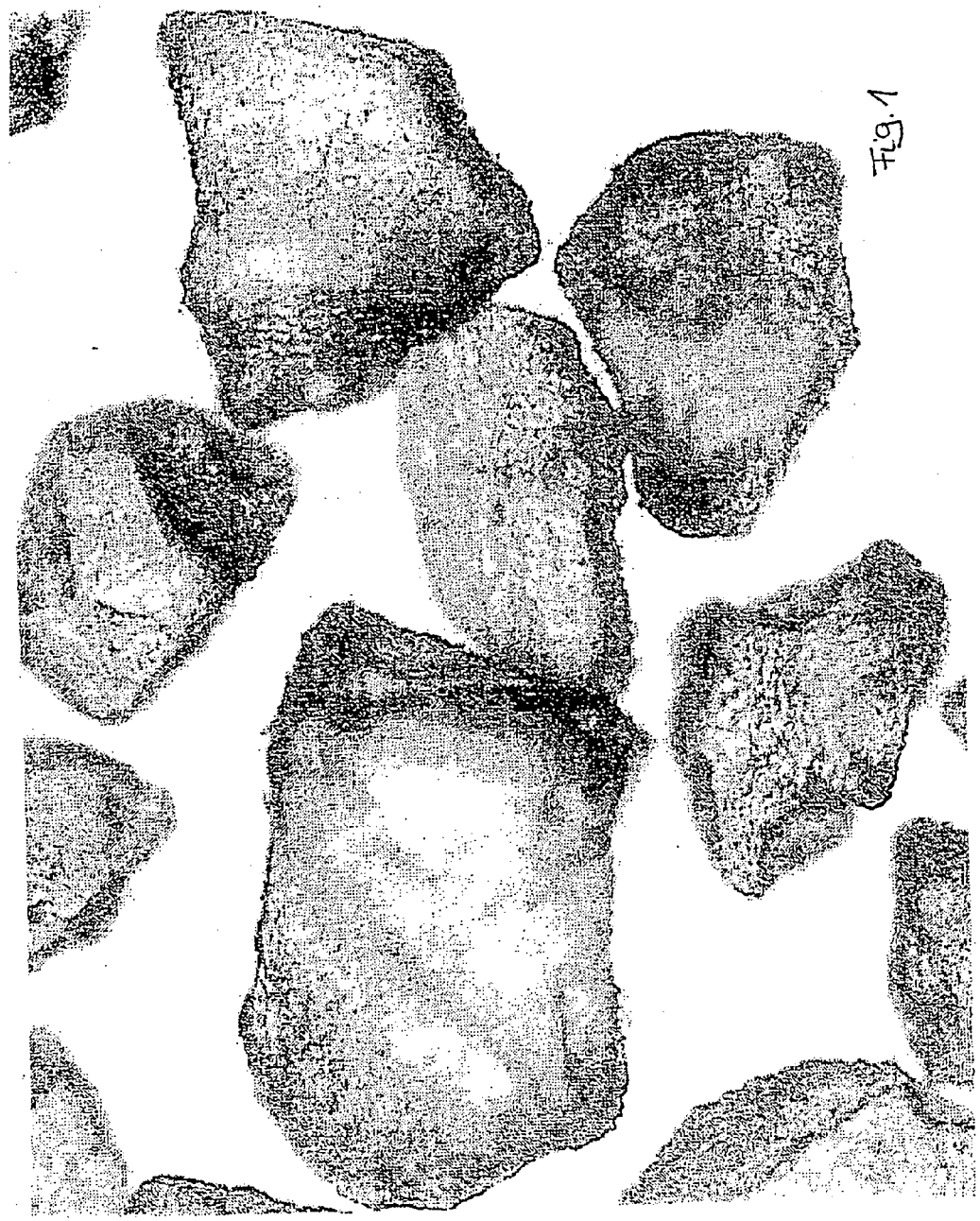
FIG. 1 shows different granulate particles.
Figure 2:
FIG. 2 shows an enlargement of a granulate particle coated with zeolite.

The products clearly no longer contain any fines after they are removed from the mixer, i.e. the zeolites appear to be completely absorbed by the granulate. Microscopic photographs of the products confirm this impression, as can be seen clearly in FIG. 2. The thick coating of zeolite particles on the surface of the co-polyamide granulate can be seen clearly.

The characteristics of the zeolites are as follows:
Flavith S108 (Product A):
$SiO_2$ content 6.9%, bulk density 545 g/liter,
Abscents 3000 (Product B):
$SiO_2$ content 7.3%, bulk density 530 g/liter.

To check the odor suppression ability of mixtures of an SAP and thermoplastics coated with the zeolites, different mixtures were produced. The odor suppression with furfural mercaptan as the test substance, with 5 to 10% odor suppressant added (Product A or Product B) to the SAP I was very good on the average. If one compares products with 0.5% Abscents 3000 on an SAP II with SAP mixtures plus 5% Product B, the odor suppression capability is comparable. Both the weighed-in quantities of the products contain the same amount of zeolite.

In the laboratory test samples, SAP I plus product A or B could not be separated by transportation or mechanical vibration. Similarly, no inhomogeneity was apparent in the finished air-laids when metering the mixtures in the air-laying apparatus.

The mixtures produced from 5 and 10% product B plus SAP I showed comparable results to SAP I in the finished air-laids with respect to infiltration time and rewetting characteristics.

What is claimed is:

1. An odor adsorption agent for use in hygiene articles configured to collect body fluids, comprising thermoplastic granulate particles and particles of zeolites directly fused to the thermoplastic granulate particles, wherein the particles of zeolites are smaller than the particles of thermoplastic granulate, and wherein odor adsorption characteristics of the zeolite particles are maintained.

2. The odor adsorption agent from claim 1, wherein the thermoplastic granulate consists of at least one of the group of polypropylenes, polyamides, polyethylenes and ethylene vinyl acetates.

3. The odor adsorption agent from claim 1, wherein the thermoplastic granulate has a particle size from 50 to 200 μm.

4. The odor adsorption agent from claim 1, wherein zeolites are in powder form and have a particle size from 0.1 to 50 μm.

5. The odor adsorption agent from claim 4, wherein zeolites are in powder form and have a particle size from 1 to 10 μm.

6. A method for producing an odor-adsorbing agent according to claim 1 comprising the steps of:
   superficially softening thermoplastic granulate particles in a heatable mixer to produce a softened hull on the respective thermoplastic granulate particles;
   metering zeolite particles into contact with the superficially softened thermoplastic granulate particles such that the zeolite particles adhere to the softened hulls of the thermoplastic granulate particles to form individual thermoplastic granulate particles with particles of zeolite bonded thereto by means of fusible bonds, wherein the particles of zeolites are smaller than the particles of thermoplastic granulate and wherein the odor adsorption characteristics of the zeolite are maintained.

7. The method for producing an odor adsorbing agent of claim 6 further comprising the step of:
   cooling the superficially softened thermoplastic granulate particles with zeolite particles adhering thereon with continued mixing motion until the surface of the thermoplastic granulate particles is essentially hardened, the cooling and mixing motion sufficient to prevent the thermoplastic granulate particles from adhering to one another.

8. The odor adsorbing agent from claim 1 wherein the thermoplastic granulate has a particle size from 100 to 1000 μm.

9. The odor adsorbing agent from claim 1 wherein the thermoplastic granulate has a particle size from 200 to 800 μm.

10. An odor adsorption agent for use for use in hygiene articles comprising:
    individual thermoplastic granules, the thermoplastic granules having an outer hull surface; and
    particles of zeolites directly fused to the outer hull surface of the individual thermoplastic granules by means of fusible bonds between the outer hull surface and the zeolite particles;
    wherein the particles of zeolites are smaller than the thermoplastic granules and the odor adsorption characteristics of the zeolite are maintained.

11. The odor adsorption agent of claim 10 wherein the thermoplastic granules have a first size and the zeolites have a second size, wherein the first size is 10 times greater than the second size.

12. The odor adsorption agent of claim 10 wherein the first size is more than one hundred times the size of the second size.

13. The odor adsorption agent of claim 10 wherein the thermoplastic granules have size between 100 to 1000 μm and the zeolites have a particle size between 0.1 μm and 50 μm.

14. The odor adsorption agent of claim 13 wherein the thermoplastic granules have a particle size between 200 and 800 μm and the zeolites have a particles size between 1 μm and 20 μm.

15. A hygiene article comprising an odor adsorption agent, the odor adsorption agent consisting of thermoplastic granulate particles and particles of zeolites directly fused to the thermoplastic granulate, wherein the particles of zeolites are smaller than the particles of thermoplastic granulate and wherein odor adsorption characteristics of the zeolite are maintained.

16. The hygiene article from claim 15, wherein the hygiene article comprises an absorbent structure which has a superabsorbent polymer as the absorption agent for fluids to be retained.

17. The hygiene article from claim 16, wherein the superabsorbent polymer and the odor adsorption agent are present as a mixture in the hygiene article.

18. The hygiene article from claim 16, wherein the superabsorbent polymer and the odor adsorbing agent are disposed in layers in the hygiene article.

19. The hygiene article from claim 15, wherein the particle size of the superabsorbent polymer and of the odor adsorption agent are essentially the same.

* * * * *